United States Patent [19]

Shaw

[11] 4,215,687
[45] Aug. 5, 1980

[54] BODY OR LIMB ENCIRCLING THERAPEUTIC DEVICE

[76] Inventor: Frank D. Shaw, 18 Oakwood La., Rumson, N.J. 07760

[21] Appl. No.: 902,179

[22] Filed: May 2, 1978

[51] Int. Cl.² .............................................. A61F 13/00
[52] U.S. Cl. .................................... 128/169; 128/165;
 128/DIG. 15
[58] Field of Search ....... 128/165, 169, 166, DIG. 15, 128/78, 80 C, 80 R, 87

[56] References Cited

U.S. PATENT DOCUMENTS

| 949,716 | 2/1910 | Quenzer | 128/169 |
|---|---|---|---|
| 3,298,366 | 1/1967 | Moore et al. | 128/169 |
| 3,469,268 | 9/1969 | Phillips | 128/87 R |
| 3,845,769 | 11/1974 | Shaw | 128/165 |

Primary Examiner—Robert W. Michell
Assistant Examiner—Thomas J. Wallen

Attorney, Agent, or Firm—Brumbaugh, Graves, Donohue & Raymond

[57] ABSTRACT

A combination or kit for making a body or limb encircling therapeutic device which includes a plurality of body or limb encircling bands, each individually adjustable for length to apply the desired pressure or provide desired support to the body or limb of humans or animals and a band anchoring tape long enough to bridge two or more adjacent bands and to maintain them in proper edge-to-edge relationship. The combination or kit also includes a plurality of splicing elements having an interlocking fabric material on one surface which interlocks with interlocking fabric on the outer surface of the band and on one surface of the anchoring tape so that in the event it is necessary to cut the band angularly to obtain conformity of the band with body or limb contour to shorten the band by removing a span thereof, the band ends with the band anchoring tape between them can be locked together by the application of the splicing element.

10 Claims, 8 Drawing Figures

BODY OR LIMB ENCIRCLING THERAPEUTIC DEVICE

This invention relates to body or limb encircling therapeutic devices and, more particularly, to a combination of cooperating elements which may be made available preassembled or in kits and utilized to construct such body or limb encircling therapeutic devices on persons or animals suffering from disorders such as lymphedema, phlebitis, varicose veins, burns, post-fracture and injury edema, stasis ulcers, obesity and circulatory disorders requiring treatment by the wearing of such therapeutic devices which apply a compressive force on or support to the body or limb.

Such of these disorders as require compressive force application have previously been treated, inter alia, by the application of elastic stockings or sleeves, spirally wound bandages, such as the Ace bandage, brace bandages, molded plaster casts and therapeutic boots. Illustrations of some of the prior art devices are those disclosed in U.S. Pat. Nos. 2,574,873, issued Nov. 13, 1951; 3,209,517, issued Oct. 5, 1965; 3,780,731, issued Dec. 25, 1973; 3,845,769, issued Nov. 5, 1974; and 3,856,008, issued Dec. 24, 1974.

Elastic materials, such as support stockings, Ace bandages and the like have the disadvantage of not presenting adjustable and either uniform or gradient pressure to the affected areas.

A custom-made non-adjustable uniform or gradient pressure can be initially built into a stocking, but that requires considerable time and skill. In the case of elastic materials, the pressure and consequently the therapeutic effects are, by the inherent characteristic of the elastic material, reduced in proportion to the reduction in size of swelling of the limb. Thus, the therapeutic values of the elastic stocking or sleeve are compromised.

If the desired therapeutic effects are to be maintained, the elastic stocking or sleeve must be replaced when significant size or swelling changes take place. The Ace-type and brace bandages must be unwrapped and rewrapped to obtain changes in applied pressure. Elastic stockings and Ace-type bandages lose elasticity due to repeated stretching, attack by body chemicals and frequent washings.

Unyielding sleeves, such as thin casts of bandage impregnated with materials which harden on drying or exposure to air, e.g., plaster casts, require skilled application by a doctor and have serious disadvantageous side effects of chafing and irritating the skin of the patient and difficulty or removal, unadjustability and lack of ventilation of the cast.

The therapeutic boot of my earlier patent, U.S. Pat. No. 3,845,769, embodied a split sleeve or boot partially encircling the limb and tightened by a plurality of overlapping bands of interlocking fabric material, such as Velcro or Scotchmate. The results and benefits of the therapeutic boot or sleeve disclosed in my prior patent can be achieved without the boot or sleeve by the lightweight, easy to construct and adjustable therapeutic device of the present invention that can be readily constructed directly on the patient by the doctor or other less skilled person.

The present invention permits the construction and application of a therapeutic device of adjustable uniform or gradient pressure to the afflicted area with minimum discomfort to the wearer and which does not require for its construction a large number of body or limb measurements requiring considerable skill.

Other advantages of the pressure applying therapeutic device of the present invention are that it does not require replacement due to inherent pressure reduction if the therapeutic effects of the applied pressure succeed in reducing the size of swelling under treatment, or in the event of increased swelling or due to change in limb size or loss of elasticity of the material.

The combination or kit for making the therapeutic device of the present invention includes a plurality of body or limb encircling bands, each individually tightened to apply the desired pressure to the body or limb, and an anchoring tape having an interlocking fabric material on one side maintaining adjacent bands of the therapeutic device in their proper edge-to-edge relationship either by direct contact with the bands or by indirect contact through splicing means having an interlocking fabric material on one surface which interlocks with the interlocking fabric material on the outer surfaces of the bands and the outer surface of the band anchoring tape.

The body or limb encircling bands require splicing when they are too long for the body or limb to be encircled or when the portion of the body or limb is contoured so that the circumferences of the body or limb engaged by the upper and lower edges of a band are significantly different so that excess has to be removed by angularly cutting the band to remove the excess material. For example, below the calf of the leg the circumference of the leg reduces sharply so that the upper edge of a band may be in tight engagement with the leg and the lower edge may be in loose engagement therewith. By angularly cutting the band to remove a wedge shaped piece of the band, this can be corrected, but the band will require splicing.

For a complete understanding of the present invention, reference can be made to the detailed description which follows and to the accompanying drawings in which.

Figure 1:
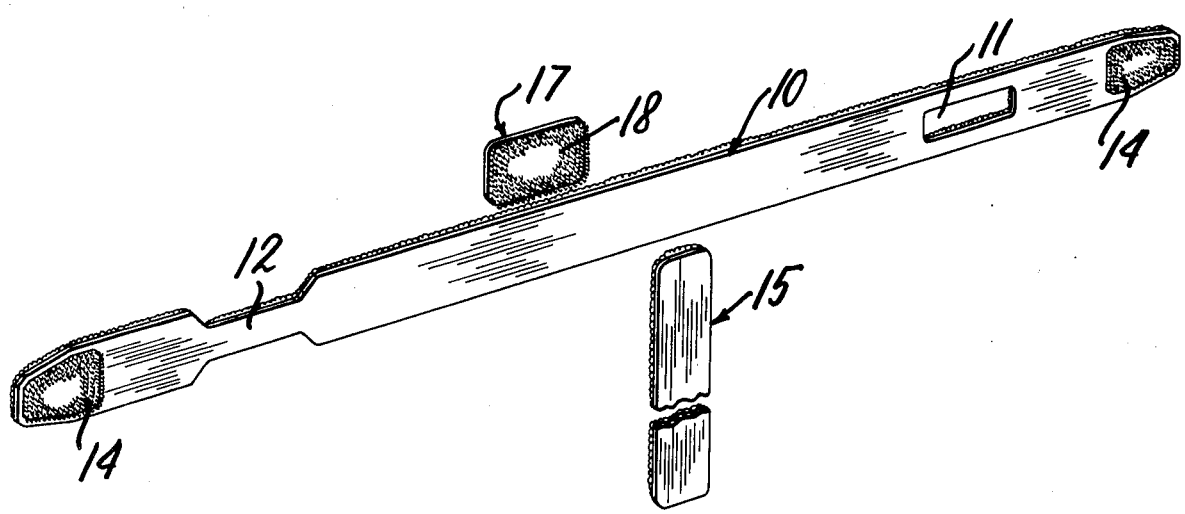
FIG. 1 is an isometric view showing the components of the present invention, namely, a band for encircling the body or limb, a band anchoring tape and a band splicing element.

As shown in FIG. 1, the present invention comprises a combination for making a compressive therapeutic body or limb encircling device which may be acquired element by element, made available in kit form or preassembled. The elements are designed to cooperate to make any of a number of compressive therapeutic body or limb encircling devices, inter alia, any of the devices illustrated in FIGS. 4, 5 or 6.

One of the components is the body or limb encircling band 10 having an opening 11 at one end and a narrow length 12 at the other end which is accommodated in the opening when it is properly applied. The length of the band 10 may be longer than the circumference of the body or limb about which it is wrapped, but because the band can be adjusted as to length and body or limb contour by removing an intermediate span, the bands may be produced in standard lengths long enough to wrap around the largest body or limb about which it is intended to be wrapped. The bands may be made available in various widths, but a width of about 1½ inches is generally satisfactory.

The band is preferably made of a strong flexible and non-stretchable material, although in some applications it may be desirable to utilize an elastic material. The inner surface is preferably relatively smooth to engage the skin or a stocking. The outer surface of the band carries an interlocking fabric material, preferably an interlocking nap material 13, such as Velcro or Scotchmate, secured to the surface of the band by any suitable means, such as by an adhesive or by stitching. As shown, it is applied continuously along the outer surface, that is to say, the surface opposite the surface which interfaces with the body. The band itself may be made of interlocking fabric material, such as Velcro or Scotchmate material. If a stretchable band were used, the interlocking fabric would not be applied continuously along the entire outer surface of the band because the nap material is not stretchable.

Figure 4:
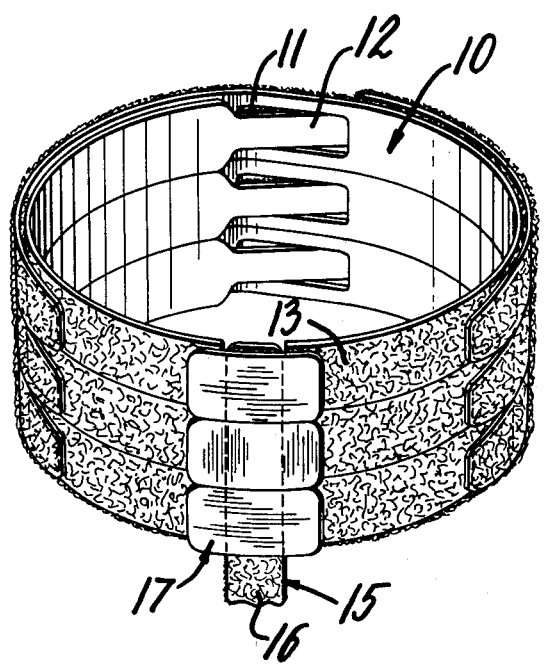
FIG. 4 is a perspective view of a body or limb encircling therapeutic device of the type shown in FIG. 3 as it would be applied to the body or limb.

The extreme ends of the inner surface of the band 10 carry pieces or patches of interlocking fabric material, preferably hook surfaces 14 which interlock with the nap surface 13 on the outer surface of the band. Thus, when the band is wrapped around the body or limb by inserting one leading end thereof through the opening 11 in the opposite end of the band, and the ends are drawn apart to tighten the band, as shown in FIG. 4, the band can be locked in the tightened condition by pressing the hook patches 14 against the underlying nap surfaces 13 of the band. In the tightened condition the narrow portion of the band should be accommodated within the opening 11.

Another component of the present invention is the band anchoring tape 15, the purpose of which is to bridge two or more adjacent bands 10 and hold them in the desired edge-to-edge relationship so that gaps do not develop between adjacent bands. If such gaps were to develop, the therapeutic compressive action of the band on that area would be compromised. The tape 15 as supplied can be of any length and cut to the desired lengths as needed. It is preferably made of the same material as the inner skin contacting surface of the band 10 and provided with an interlocking fabric material, preferably the nap material 16 that is carried by the outer surface of the band 10, but alternatively the hook material 16 for use in the application shown in FIG. 5.

Another useful component of the invention is the splicing element 17, also preferably made of the same material as the band 10, and carrying an interlocking fabric material 18 on one surface thereof, preferably a hook-type interlocking fabric that interlocks with a nap-type interlocking fabric upon the application of a pressure between the two surfaces.

When it is necessary to cut the band angularly to obtain conformity of the band to body or limb contour, or when the band 10 is too long for the body or limb about which it is to be aplied, an intermediate span of the band is removed to decrease the length of the band to a suitable length. The ends of the band can then be spliced together by the application of one of the band splicing elements 17 to the outer nap surfaces 13 of the bands ends to be spliced and to the outer surface of band anchoring tape 15, as shown in FIG. 2.

Figure 2:
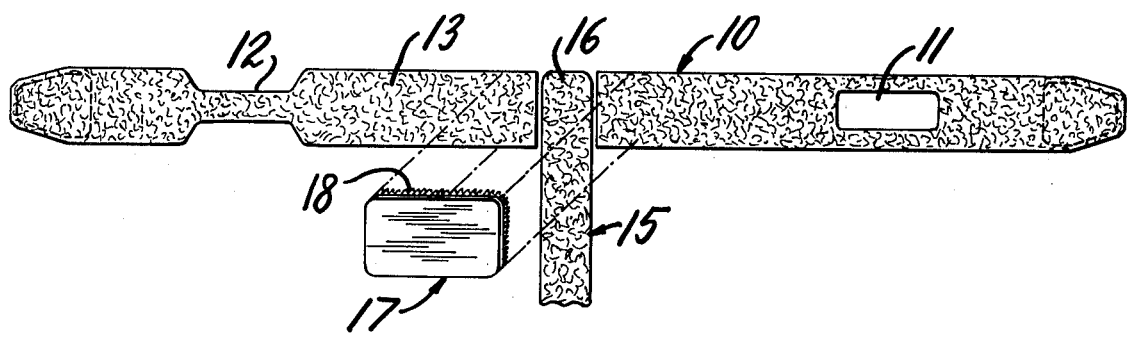
FIG. 2 is an exterior elevational view showing the band for encircling the body or limb with an intermediate section removed, an end of the band anchoring tape accommodated between the end sections of the band and a splicing element for joining the band sections and the band anchoring tape.

One example of utilizing the three components 10, 15 and 17 together in making a therapeutic device is illustrated in FIG. 2 of the drawings. As shown therein, a center span of band 10 has been removed to shorten the band to the desired length and the bridging tape 15 is placed perpendicularly between the ends of the band 10 to be spliced together with the outer nap surfaces 13 and 16 of the band and tape facing outwardly away from the portion of the body to which the band is to be applied. The hook surface 18 of the splicing element 17 is then applied across the outer nap surfaces 13 of the band ends to be spliced and to the nap surface of the intermediate band anchoring tape 15, so as to lock them together as a composite unit.

Figure 3:
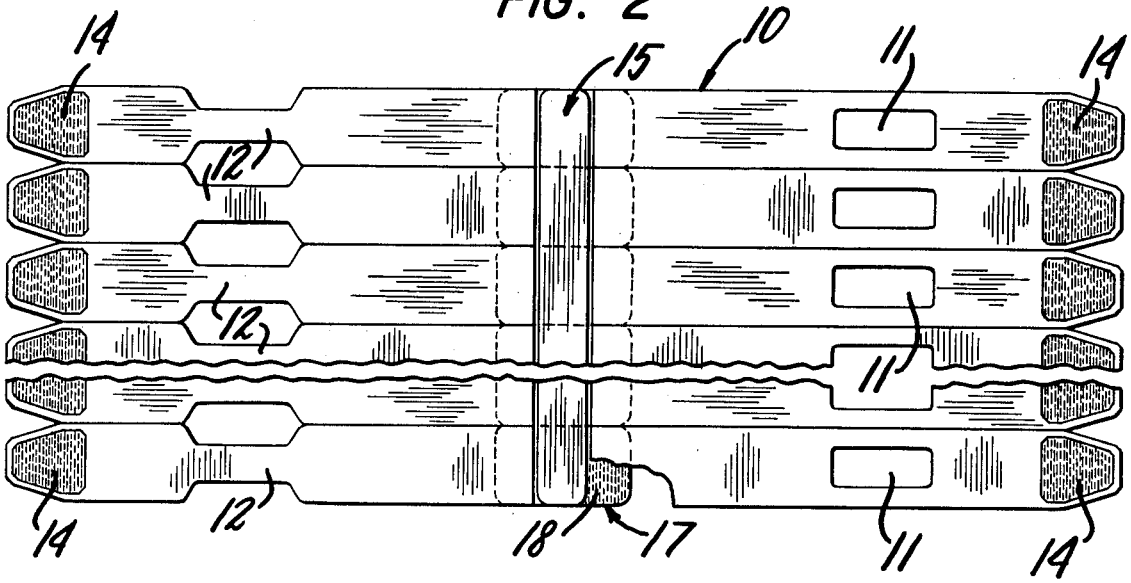
FIG. 3 is an interior elevational view of a body or limb encircling therapeutic device made from the components shown in FIGS. 1 and 2.

A therapeutic device, shown in FIG. 3, can be made by placing a plurality of spliced bands 10 edge-to-edge, utilizing a band anchoring tape 15 long enough to bridge the desired number of bands together to cover the length of the body to receive the therapeutic treatment and applying a splicing element 17 at each juncture. The device can be applied to the body or limb, as shown in FIG. 4, by placing the bands around the body or limb in the area to receive the compressive therapeutic treatment. Each band can be separately tightened and secured as described above.

Figure 4A:
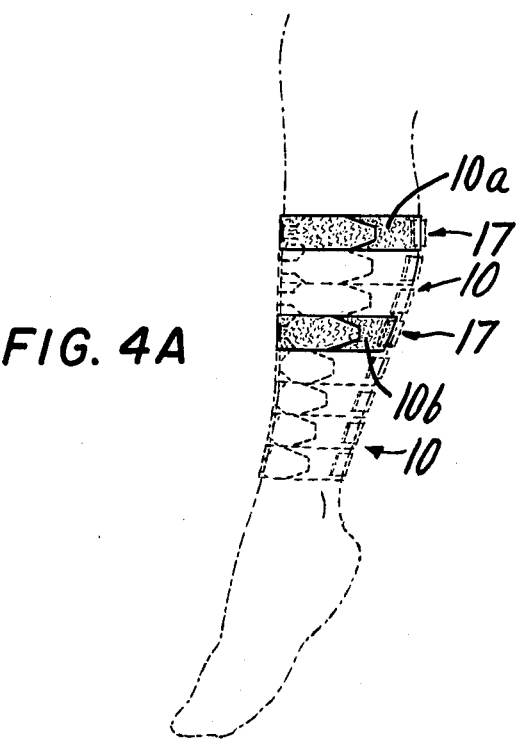
FIG. 4A is a view of a limb showing a pair of bands 10a and 10b, the latter requiring cutting on a greater angle in splicing than the former to compensate for the greater change in the contour of the part of the limb to which it is applied.
Figure 4B:
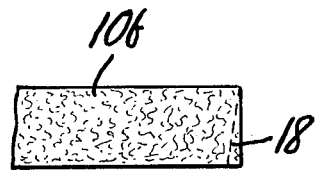
FIG. 4B is a view showing an angular or bias cut of the band necessary to compensate for the change in contour of the limb.

It is sometimes necessary to cut the band edges to be spliced together on an angle or bias 18 (see FIG. 4B) to remove excess material and cause them to abut edge-to-edge with opposite edges of the band anchoring tape 15. This is encountered where the body increases or decreases in girth and one edge of a band 10 is in tight engagement with the circumference of the body and the other edge of the band is in loose engagement with the body. This can be corrected by cutting the edges of the bands to be spliced on a bias, removing the surplus material from the loose edge and causing the biased edges to abut with the edges of the band anchoring tape 15. In the illustration shown in FIG. 4A, the lower band 10b will require a greater bias cut to abut with the edge of the band anchoring tape 15 than the upper band 10a.

If the bands are initially of a length within the range that they can be applied to the body or limb without removing a center span, and body or limb contour does not require that the bands be angularly cut, they can be applied without need to splice ends together by use of the splicing elements 17. A therapeutic device of this type is illustrated in FIG. 5 of the drawings where the band anchoring tape 15 is provided with a hook-type interlocking fabric surface 16' to adhere directly to the outer nap surfaces 13 of the bands to hold the bands in edge-to-edge relationship by bridging the entire group of bands comprising the therapeutic device.

Figure 5:
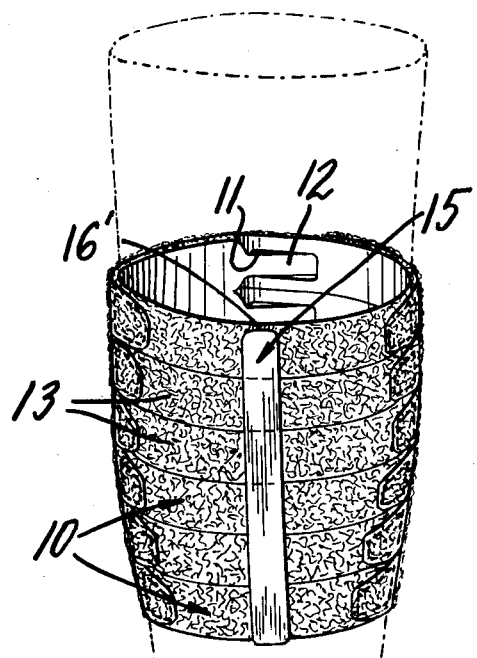
FIG. 5 is another body or limb encircling therapeutic device applied to a limb in an application without the the band splicing elements as shown from the rear of the limb.

The FIG. 5 embodiment of the therapeutic device can also be utilized on portions of the body where the body contour requires that the bands be angularly cut, for example, the lower portion of the leg between the ankle and the calf. The excess material can be removed from the one edge of the band by removing a wedge-shaped portion from the band by making two angular cuts of the type illustrated in FIG. 4B so that the remaining edges of the band can be spliced together in edge-to-edge relationship by the vertical tape 16'. With the wedge-shaped portion thus removed, the band will uniformly engage the leg from upper to lower edge and the tape 16' will serve the dual purpose of splicing the ends of the band together in edge-to-edge relationship and maintaining adjacent bands in proper edge-to-edge relationship.

Figure 6:
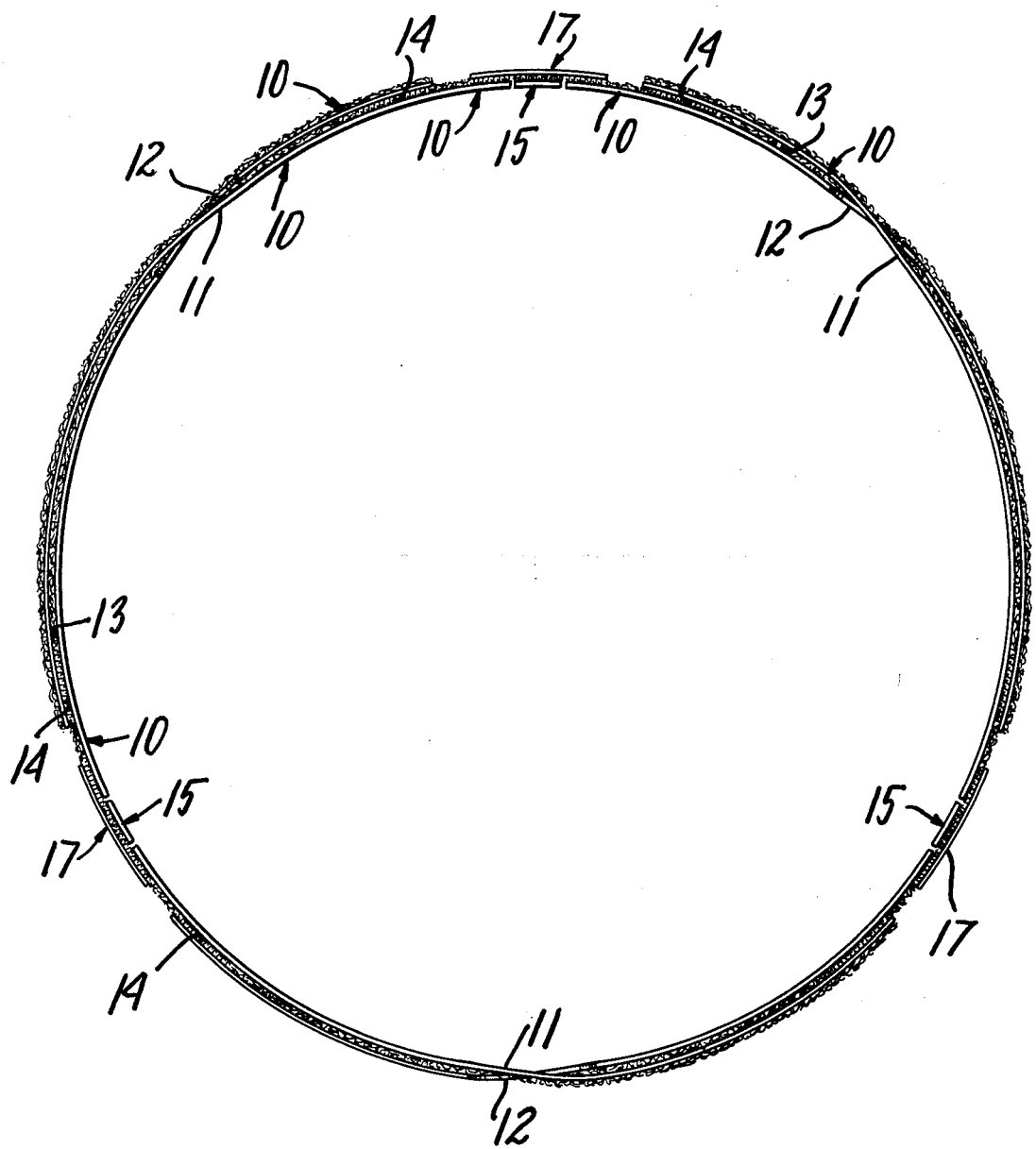
FIG. 6 is a plan view of a body encircling therapeutic device utilizing the components of the present invention.

For a body or limb of large circumference, more than a single spliced band 10 can be utilized. For example, as shown in FIG. 6, a therapeutic device is shown having three splices of the type illustrated in FIG. 2 around its circumference. At intervals of 120° apart, one of the splicing elements 17 bridges a pair of band ends and an intermediate band anchoring tape 15 bridging a plurality of parallel bands. If body or limb contours do not require angle cuts of bands 10, splicing elements may be omitted and the FIG. 5 band bridging tape may be employed to anchor the bands in side-by-side relationship.

Any one of the above described body or limb encircling devices, and others, can be readily constructed and applied directly on the patient by the doctor or by a relatively unskilled person having a minimum of instruction. Once applied, the device can be tightened or loosened band-by-band in an instant to change the pressure applied by the band. The device, in comparison with prior art devices, is more comfortable, light in weight and less unwieldy. It can be quickly taken off for washing the device or bathing the wearer and easily replaced.

The invention has been shown and described in preferred embodiments and by way of example; nevertheless, various variations and modifications can be made therein without departing from the spirit of the invention. For example, the splicing elements and band anchoring tapes may be supplied in roll or long length and cut to suitable lengths as needed. The invention, therefore, is not to be limited to any particular form or embodiment, except insofar as such form or embodiment is expressly specified in the appended claims.

I claim:

1. A combination for making a body or limb encircling therapeutic device comprising a plurality of body or limb encircling bands in which intermediate portions are removed to decrease the lengths of the bands and to leave pairs of edges to be spliced, one end of each band including an opening for the insertion of the other end and the said other end including a narrow length in the band to be received in the opening, said threaded band ends being capable of tightening the band around the body or limb, interlocking fabric means on the outer surface of each band and on the inner surfaces of the band ends to secure the band in its tightened condition, a flexible and unsupported band anchoring tape extending longitudinally of the body or limb intermediate the band edges to be spliced, band splicing means interfacing with the outer surfaces of the bands adjacent the edges to be spliced and with the outer surface of the intermediate band anchoring tape, the edges of the intermediate band ends to be spliced being cut to be in substantially edge-to-edge relationship and without overlap with the longitudinal edges of the band anchoring tape to maintain adjacent body or limb encircling bands in substantially edge-to-edge relationship and without overlap so that one band can be adjusted independently of adjacent bands, and interlocking fabric means for anchoring the inner surface of said band splicing means with the outer surface of said band anchoring tape and the outer surfaces of the bands adjacent the edges to be spliced leaving the bands throughout the greater portion of their lengths on both sides of said band anchoring tape separate from each other so that each band can be adjusted independently of the other.

2. A combination as set forth in claim 1 in which the intermediate band edges to be spliced are cut on a bias to extend substantially parallel to the adjacent longitudinally extending edge of the band anchoring tape, the angle of bias being such as to change the respective lengths of the opposite circumferential edges of the bands to cause the band to uniformly engage a surface of the body of changing circumference while causing the band to be in substantially edge-to-edge relationship with an adjacent band.

3. A combination as set forth in claim 1 in which at least one of the bands includes at least two pairs of band ends, each pair including one band end having an opening receiving the narrow length of the other band end threaded therethrough, said band splicing means connecting said pairs of bands ends seriatim so that the tightness of the band can be adjusted by separating either pair of band ends and securing them together again.

4. A combination as set forth in claim 3 in which the band anchoring tape extends perpendicularly to the band portion and intermediate the band portions spliced together by the band splicing means, the band splicing means interlocking with surfaces of the band portions and the intermediate band anchoring tape to lock them together in a composite assembly.

5. A combination for making a body or limb encircling therapeutic device comprising a plurality of body or limb encircling bands adapted to be wrapped around the body or limb and tightened and secured, interlocking fabric means for securing the ends of each band to the outer surface thereof when tightly wrapped around the body or limb, band splicing means for splicing a pair of band ends together when a portion of the band has been removed, interlocking fabric means on the outer surface of the band ends to be spliced and on an interfacing surface of the band splicing means, a flexible and unsupported band anchoring tape adapted to be placed longitudinally intermediate the band ends to be spliced, the edges of the band ends to be spliced being angled to insure that the edges of the band ends to be spliced extend parallel in substantially edge-to-edge relationship with the longitudinal edges of the band anchoring tape and that the circumferential edges of adjacent body or limb encircling bands extend parallel in subtantially edge-to-edge relationship without overlap and interlocking fabric means on the outer surface of said band anchoring tape to interface with the interlocking fabric means on the band splicing means to interlock therewith, adjacent bands being separate from each other throughout the greater portion of their lengths on both sides of said band anchoring tape so that each band can be adjusted independently of the other.

6. A combination as set forth in claim 5 in which at least one of the body or limb encircling bands includes at least two pairs of band ends connected seriatim so that the tightness of the band can be adjusted by separating either pair and securing them together again.

7. A method for making a body or limb encircling therapeutic device comprising the steps of encircling the body or limb to be treated with a plurality of body or limb encircling bands in substantially edge-to-edge relationship without overlap, one end of each band including an opening for the insertion of the other end and the said other end including a narrow length in the band to be received in the opening, threading the narrow length of one end in the opening of the other end and securing the band around the body or limb, securing the bands by interlocking fabric means on the outer surface of each band and on the inner surfaces of the band ends, removing intermediate spans from the bands to form intermediate band ends to be spliced, applying a band anchoring tape in a direction perpendicularly to the body or limb encircling bands, biasing the edges of the band ends to be spliced to maintain adjacent body or limb encircling bands in substantially edge-to-edge relationship and to maintain the said edges in substantially edge-to-edge relationship with the longitudinal edges of the band anchoring tape and applying a band splice having interlocking fabric means on the inner surface against interlocking fabric means on the outer surface of said band anchoring tape and the outer surfaces of said band ends to be spliced, adjacent bands being separate from each other throughout the greater portion of their lengths on both sides of said band anchoring tape so that each band can be adjusted independently of the other.

8. A method as set forth in claim 7 including connecting at least a pair of body or limb encircling bands end-to-end and securing them in end-to-end relationship by interlocking fabric means.

9. A method as set forth in claim 7 including the step of removing a wedge-shaped portion from a band encircling a portion of the body or limb of changing circumference so as to remove the excess portion of the band from the region of smaller circumference and cause the band to more uniformly engage the surface of the body or limb.

10. A method of making a body or limb encircling therapeutic device comprising the steps of encircling the body or limb to be treated with a plurality of body or limb encircling bands in substantially edge-to-edge relationship without overlap, removing the excess material from a band encircling a portion of the body or limb where the circumference changes from one edge of the band to the other to form intermediate band ends to be spliced, applying a band anchoring tape in a direction longitudinally of the body or limb, biasing the edges of the band ends to be spliced to insure that the band engages the body or limb uniformly and lies in edge-to-edge relationship with an adjacent band without overlap and to insure that the biased edges lie in substantially edge-to-edge relationship with the longitudinal edges of the band anchoring tape, splicing the band from which the excess material has been removed by applying a band splice in interfacing relation with the outer surfaces of the band anchoring tape and the band edges to be spliced and secured thereto by interlocking fabrics, thereby maintaining portions of adjacent bands intermediate their ends in substantially edge-to-edge relationship without overlap while leaving the bands separated from each other throughout their lengths on both sides of said portions intermediate their ends.

* * * * *